(12) United States Patent
Kim et al.

(10) Patent No.: US 12,097,276 B2
(45) Date of Patent: Sep. 24, 2024

(54) COSMETIC COMPOSITION COMPRISING THEASINENSIN A

(71) Applicants: AMOREPACIFIC CORPORATION, Seoul (KR); SEOUL NATIONAL UNIVERSITY R&DB FOUNDATION, Seoul (KR)

(72) Inventors: Eun Mi Kim, Yongin-si (KR); Kyeonghwan Hwang, Yongin-si (KR); Dong Hyun Kim, Yongin-si (KR); Byung-Gee Kim, Seoul (KR); Jinkyung Choi, Seoul (KR)

(73) Assignees: AMOREPACIFIC CORPORATION, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 665 days.

(21) Appl. No.: 17/289,105

(22) PCT Filed: Nov. 6, 2019

(86) PCT No.: PCT/KR2019/014980
§ 371 (c)(1),
(2) Date: Apr. 27, 2021

(87) PCT Pub. No.: WO2020/096348
PCT Pub. Date: May 14, 2020

(65) Prior Publication Data
US 2022/0000742 A1    Jan. 6, 2022

(30) Foreign Application Priority Data

Nov. 6, 2018 (KR) .................. 10-2018-0135031

(51) Int. Cl.
*A61K 8/49* (2006.01)
*A61Q 19/02* (2006.01)
*A61Q 19/08* (2006.01)

(52) U.S. Cl.
CPC ............. *A61K 8/498* (2013.01); *A61Q 19/02* (2013.01); *A61Q 19/08* (2013.01); *A61K 2800/522* (2013.01)

(58) Field of Classification Search
CPC .. A61K 8/498; A61K 2800/522; A61Q 19/02; A61Q 19/08
See application file for complete search history.

(56) References Cited

U.S. PATENT DOCUMENTS

2008/0275258 A1    11/2008    Nakai et al.
2015/0140141 A1*   5/2015     Milow ................. A61K 8/9706
                                                               424/769

FOREIGN PATENT DOCUMENTS

| JP | 2000-226329 A | 8/2000 |
| JP | 2007-119412 A | 5/2007 |
| JP | 2010-090058 A | 4/2010 |
| JP | 4507027 B2 | 7/2010 |
| JP | 2012-135227 A | 7/2012 |
| KR | 10-1077802 B1 | 10/2011 |
| KR | 10-2014-0048177 A | 4/2014 |
| WO | 2014/136681 A1 | 9/2014 |

OTHER PUBLICATIONS

Vippagunta et al., 48 Adv. Drug Del. Rev. 3 (Year: 2001).*
Xiao-Feng Deng et al., "Mechanisms of efficacies of epigallocatechin gallate in cosmetics", China Surfactant Detergent & Cosmetics, 2015, vol. 45, No. 10, pp. 589-592 (4 pages total).
Office Action dated Nov. 2, 2022 issued by the Chinese Patent Office in Chinese Application No. 201980070536.1.
Monthana Weerawatanakorn et al., "Chemistry and health beneficial effects of oolong tea and theasinensins", Food Science and Human Wellness, 2015, pp. 133-146, vol. 4.
Hye-Won Lee et al., "Optimization for theasinensin A production by extracellular enzymes of Aspergillus niger", The Korean Society for Biotechnology and Bioengineering International Academia-Industry Joint Meeting, Oct. 10-12, 2018.
Ayami Hisanaga et al., "Anti-inflammatory activity and molecular mechanism of Oolong tea theasinensin", Food & Function, Jun. 2014, pp. 1891-1897, vol. 5.
Ju Qiu et al., "Stimulation of glucose uptake by theasinensins through the AMP-activated protein kinase pathway in rat skeletal muscle cells", Biochemical Pharmacology, 2014, pp. 344-351, vol. 87.
Charles E. Isaacs et al., "Digallate Dimers of (-)-Epigallocatechin Gallate Inactivate Herpes Simplex Virus", Antimicrobial Agents and Chemotherapy, Dec. 2011, pp. 5646-5653, vol. 55, No. 12.
Jian Guo et al., "Evaluating the Reduced Hydrophobic Taste Sensor Response of Dipeptides by Theasinensin A by Using NMR and Quantum Mechanical Analyses", PLOS ONE, Jun. 16, 2016, pp. 1-14.
Wei Zhu et al., "A-type ECG and EGCG dimers inhibit 3T3-L1 differentiation by binding to cholesterol in lipid rafts", Journal of Nutritional Biochemistry, 2017, pp. 62-73, vol. 48.
International Searching Authority, International Search Report of PCT/KR2019/014980 date Feb. 7, 2020 [PCT/ISA/210].

* cited by examiner

*Primary Examiner* — Sean M Basquill
(74) *Attorney, Agent, or Firm* — Sughrue Mion, PLLC (57) ABSTRACT

A composition contains, as an effective component, theasinensin A, an enantiomer thereof, a pharmaceutically acceptable salt thereof, a hydrate thereof, or a solvate thereof. The composition has an excellent stability and provides wrinkle-reducing or skin elasticity-enhancing benefits, and skin-brightening benefits by containing theasinensin A, an enantiomer thereof, a pharmaceutically acceptable salt thereof, a hydrate thereof, or a solvate thereof, as an effective component.

5 Claims, 8 Drawing Sheets

COSMETIC COMPOSITION COMPRISING THEASINENSIN A

CROSS REFERENCE TO RELATED APPLICATIONS

This application is a National Stage of International Application No. PCT/KR2019/014980, filed Nov. 6, 2019, claiming priority to Korean Patent Application No. 10-2018-0135031, filed Nov. 6, 2018, the contents of all of which are incorporated herein by reference in their entirety.

TECHNICAL FIELD

The present disclosure relates to a functional cosmetic composition.

BACKGROUND ART

Green tea contains a large quantity of catechins. It is known that epigallocatechin gallate (EGCG) is the most abundant. As various effects of EGCG are known, including strong antioxidant effect as well as anticancer activity, prevention of skin damage by UV, etc., researches are being conducted in the field of food, medicine and cosmetics for its application. However, there is difficulty in applying EGCG for products due to stability and bioavailability problems because it is not dissolved well in water and is unstable since it is easily oxidized and degraded upon exposure to external environments such as oxygen, heat, light, etc.

REFERENCES OF RELATED ART

Patent Documents (Patent document 1) Korean Patent Registration Publication No. 10-1077802.

DISCLOSURE

Technical Problem

In an aspect, the present disclosure is directed to providing a cosmetic composition comprising theasinensin A, which is an EGCG dimer having superior stability, as an active ingredient.

Technical Solution

In an aspect, the present disclosure provides a cosmetic composition comprising theasinensin A, an enantiomer thereof, a pharmaceutically acceptable salt thereof, a hydrate thereof or a solvate thereof as an active ingredient.

Advantageous Effects

In an aspect, the present disclosure may provide a composition having remarkably superior stability as compared to epigallocatechin gallate (EGCG) by comprising theasinensin A, which is an epigallocatechin gallate (EGCG) dimer, an enantiomer thereof, a pharmaceutically acceptable salt thereof, a hydrate thereof or a solvate thereof as an active ingredient. In addition, the present disclosure may provide a composition capable of exhibiting superior skin wrinkle-reducing or skin elasticity-enhancing effect and having superior skin-brightening effect unlike epigallocatechin gallate (EGCG) by comprising theasinensin A as an active ingredient.

BEST MODE

Hereinafter, exemplary embodiments of the present disclosure will be described in more detail referring to the attached drawings. However, the present disclosure is not limited to the exemplary embodiments described herein but may be embodied in different forms. The exemplary embodiments described herein are provided such that the disclosure is thorough and complete and fully convey the aspects of the present disclosure to those skilled in the art. In the drawings, the dimension of each element, such as width, thickness, etc., may have been exaggerated for clarity. In addition, although only a part of an element may have been shown for the convenience of explanation, those skilled in the art will easily understand the remaining part of the element. In addition, those having ordinary knowledge in the art will be able to embody the present disclosure into various other forms without departing from the scope of the present disclosure.

In the present disclosure, the term "improvement" refers to any action of ameliorating or favorably changing a target symptom by administering a composition according to an exemplary embodiment of the present disclosure.

In an exemplary embodiment, the present disclosure may provide a cosmetic composition comprising theasinensin A (TSA), an enantiomer thereof, a pharmaceutically acceptable salt thereof, a hydrate thereof or a solvate thereof as an active ingredient.

In the present disclosure, "isomers" particularly comprise not only optical isomers (e.g., essentially pure enantiomers, essentially pure diastereomers or mixtures thereof) but also conformational isomers (i.e., isomers different only in the angle of one or more chemical bonds), position isomers (particularly tautomers) or geometric isomers (e.g., cis-trans isomers).

In the present disclosure "essentially pure" means that a specific compound having enantiomers or diastereomers has a single enantiomer or diastereomer at about 90% or more, specifically about 95% or more, more specifically about 97% or more or about 98% or more, further more specifically about 99% or more, even more specifically about 99.5% or more.

In the present disclosure, "pharmaceutically acceptable" means being recognized as being able to be used for an animal, more specifically for human, by avoiding significant toxic effects when used in conventional medicinal dosages, as being approved by the government or regulatory agency equivalent or as being listed in the Pharmacopeia or other general pharmacopeias

In the present disclosure, a "pharmaceutically acceptable salt" refers to a salt according to an aspect the present disclosure which is pharmaceutically acceptable and has the desired pharmacological activity of its parent compound. The salt may comprise (1) an acid addition salt formed from an inorganic acid such as hydrochloric acid, hydrobromic acid, sulfuric acid, nitric acid, phosphoric acid, etc.; or from an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is substituted.

In the present disclosure, a "hydrate" refers to a compound to which water is bonded, and is used in a broad concept, comprising an inclusion compound without chemical bonding between the compound and water.

In the present disclosure, a "solvate" refers to a higher-order compound formed between a molecule or ion of a solute and a molecule or ion of a solvent.

In an exemplary embodiment, the theasinensin A has the molecular formula $C_{44}H_{34}O_{22}$ and has the following chemical structure.

[Chemical Formula 1]

In an exemplary embodiment, the theasinensin A is a dimer of epigallocatechin gallate (EGCG) having a chemical structure of Chemical Formula 2. Unlike epigallocatechin gallate which is comprised in green tea or green tea extract, theasinensin A is known to not be comprised in green tea or green tea extract. Whereas epigallocatechin gallate is unstable because it is easily oxidized upon exposure to external environments such as heat, light, etc., the theasinensin A exhibits superior stability because it is an oxidized form of molecule and can be stably comprised in a cosmetic composition as an active ingredient.

[Chemical Formula 2]

In an exemplary embodiment, the theasinensin A may be comprised in a composition at a higher content because it has better stability than epigallocatechin gallate. In an exemplary embodiment, the composition may comprise the active ingredient in an amount of 0.001-1.0 wt % based on the total weight of the composition. Specifically, in an exemplary embodiment, the composition may comprise the active ingredient in an amount of 0.001 wt % or more, 0.002 wt % or more, 0.003 wt % or more, 0.004 wt % or more, 0.005 wt % or more, 0.006 wt % or more, 0.007 wt % or more, 0.008 wt % or more, 0.009 wt % or more, 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more or 1.0 wt % or more based on the total weight of the composition, although not being limited thereto. In addition, in an exemplary embodiment, the composition may comprise the active ingredient in an amount of 1.0 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, 0.01 wt % or less, 0.009 wt % or less, 0.008 wt % or less, 0.007 wt % or less, 0.006 wt % or less, 0.005 wt % or less, 0.004 wt % or less, 0.003 wt % or less, 0.002 wt % or less or 0.001 wt % or less based on the total weight of the composition, although not being limited thereto.

In an exemplary embodiment, the administration dosage of the active ingredient may be from 0.1 mg/kg/day to 10 g/kg/day. In an exemplary embodiment, the administration dosage of the active ingredient may vary depending on the age, sex and body weight of a subject, a particular disease or pathological condition of the subject, the severity of the disease or pathological condition, administration route, etc. Determination of the administration dosage based on these factors is within the level of those skilled in the art. For example, the administration dosage may be 0.1 mg/kg/day or more, 0.2 mg/kg/day or more, 0.3 mg/kg/day or more, 0.4 mg/kg/day or more, 0.5 mg/kg/day or more, 0.6 mg/kg/day or more, 0.7 mg/kg/day or more, 0.8 mg/kg/day or more, 0.9 mg/kg/day or more, 1 mg/kg/day or more, 2 mg/kg/day or more, 3 mg/kg/day or more, 4 mg/kg/day or more, 5 mg/kg/day or more, 10 mg/kg/day or more, 20 mg/kg/day or more, 30 mg/kg/day or more, 40 mg/kg/day or more, 50 mg/kg/day or more, 60 mg/kg/day or more, 70 mg/kg/day or more, 80 mg/kg/day or more, 90 mg/kg/day or more, 100 mg/kg/day or more, 110 mg/kg/day or more, 120 mg/kg/day or more, 130 mg/kg/day or more, 140 mg/kg/day or more, 150 mg/kg/day or more, 160 mg/kg/day or more, 170 mg/kg/day or more, 180 mg/kg/day or more, 190 mg/kg/day or more, 200 mg/kg/day or more, 250 mg/kg/day or more, 300 mg/kg/day or more, 350 mg/kg/day or more, 400 mg/kg/day or more, 450 mg/kg/day or more, 500 mg/kg/day or more, 550 mg/kg/day or more, 600 mg/kg/day or more, 650 mg/kg/day or more, 700 mg/kg/day or more, 750 mg/kg/day or more, 800 mg/kg/day or more, 850 mg/kg/day or more, 900 mg/kg/day or more, 950 mg/kg/day or more, 1 g/kg/day or more, 2 g/kg/day or more, 3 g/kg/day or more, 4 g/kg/day or more, 5 g/kg/day or more, 6 g/kg/day or more, 7 g/kg/day or more, 8 g/kg/day or more or 9 g/kg/day or more. In addition, the administration dosage may be, for example, 10 g/kg/day or less, 9 g/kg/day or less, 8 g/kg/day or less, 7 g/kg/day or less, 6 g/kg/day or less, 5 g/kg/day or less, 4 g/kg/day or less, 3 g/kg/day or less, 2 g/kg/day or less, 1 g/kg/day or less, 500 mg/kg/day or less, 450 mg/kg/day or less, 400 mg/kg/day or less, 350 mg/kg/day or less, 300 mg/kg/day or less, 250 mg/kg/day or less, 200 mg/kg/day or less, 190 mg/kg/day or less, 180 mg/kg/day or less, 170 mg/kg/day or less, 160 mg/kg/day or less, 150 mg/kg/day or less, 140 mg/kg/day or less, 130 mg/kg/day or less, 120 mg/kg/day or less, 110 mg/kg/day or less, 100 mg/kg/day or less, 90 mg/kg/day or less, 80 mg/kg/day or less, 70 mg/kg/day or less, 60 mg/kg/day or less, 50 mg/kg/day or less, 40 mg/kg/day or less, 30 mg/kg/day or less, 20 mg/kg/day or less, 10 mg/kg/day or less, 9 mg/kg/day or less, 8 mg/kg/day or less, 7 mg/kg/day or less, 6 mg/kg/day or less, 5 mg/kg/day or less, 4 mg/kg/day or less, 3 mg/kg/day or less, 2 mg/kg/day or less or 1 mg/kg/day or less. However, the administration dosage does not limit the scope of the present disclosure in any way.

In an exemplary embodiment, the present disclosure may provide a composition for reducing skin wrinkles or enhancing skin elasticity, which comprises theasinensin A, an enantiomer thereof, a pharmaceutically acceptable salt thereof, a hydrate thereof or a solvate thereof as an active ingredient. In another exemplary embodiment, the present disclosure may provide a use of the theasinensin A, an enantiomer thereof, a pharmaceutically acceptable salt thereof, a hydrate thereof or a solvate thereof for preparation of a composition for reducing skin wrinkles or enhancing skin elasticity. In another exemplary embodiment, the present disclosure may provide a method for reducing skin wrinkles or enhancing skin elasticity, which comprises administering an effective amount of the theasinensin A, an enantiomer thereof, a pharmaceutically acceptable salt thereof, a hydrate thereof or a solvate thereof to a subject in need thereof. In another exemplary embodiment, the present disclosure may provide the theasinensin A, an enantiomer thereof, a pharmaceutically acceptable salt thereof, a hydrate thereof or a solvate thereof as an active ingredient for use in a composition for reducing skin wrinkles or enhancing skin elasticity. In addition, the present disclosure may provide a non-therapeutic use of the theasinensin A, an enantiomer thereof, a pharmaceutically acceptable salt thereof, a hydrate thereof or a solvate thereof as an active ingredient for reducing skin wrinkles or enhancing skin elasticity. The active ingredient may reduce skin wrinkles or enhance skin elasticity by inhibiting the expression of matrix metalloproteinase-1 (MMP-1). Here, the "skin" refers to the tissue covering the body surface of an animal, and is used in the broadest concept, comprising the tissue covering the surface of the face, body, etc.

In an exemplary embodiment, the present disclosure may provide a composition for brightening skin, which comprises theasinensin A, an enantiomer thereof, a pharmaceutically acceptable salt thereof, a hydrate thereof or a solvate thereof as an active ingredient. The active ingredient may provide skin-brightening effect by inhibiting melanin production, which is a novel effect not exhibited by epigallocatechin gallate. In another exemplary embodiment, the present disclosure may provide a use of the theasinensin A, an enantiomer thereof, a pharmaceutically acceptable salt thereof, a hydrate thereof or a solvate thereof for preparation of a composition for brightening skin. In another exemplary embodiment, the present disclosure may provide a method for brightening skin, which comprises administering an effective amount of the theasinensin A, an enantiomer thereof, a pharmaceutically acceptable salt thereof, a hydrate thereof or a solvate thereof to a subject in need thereof. In another exemplary embodiment, the present disclosure may provide the theasinensin A, an enantiomer thereof, a pharmaceutically acceptable salt thereof, a hydrate thereof or a solvate thereof as an active ingredient for use in a composition for brightening skin. In addition, the present disclosure may provide a non-therapeutic use of the theasinensin A, an enantiomer thereof, a pharmaceutically acceptable salt thereof, a hydrate thereof or a solvate thereof as an active ingredient for brightening skin.

In an exemplary embodiment, the present disclosure may provide a composition for antioxidation, which comprises theasinensin A, an enantiomer thereof, a pharmaceutically acceptable salt thereof, a hydrate thereof or a solvate thereof as an active ingredient. The active ingredient may provide antioxidant effect by inhibiting the activity of 2,2-diphenyl-1-picrylhydrazyl (DPPH). In another exemplary embodiment, the present disclosure may provide a use of the theasinensin A, an enantiomer thereof, a pharmaceutically acceptable salt thereof, a hydrate thereof or a solvate thereof for preparation of a composition for antioxidation. In another exemplary embodiment, the present disclosure may provide a method for antioxidation, which comprises administering an effective amount of the theasinensin A, an enantiomer thereof, a pharmaceutically acceptable salt thereof, a hydrate thereof or a solvate thereof to a subject in need thereof. In another exemplary embodiment, the present disclosure may provide the theasinensin A, an enantiomer thereof, a pharmaceutically acceptable salt thereof, a hydrate thereof or a solvate thereof as an active ingredient for use in a composition for antioxidation. In addition, the present disclosure may provide a non-therapeutic use of the theasinensin A, an enantiomer thereof, a pharmaceutically acceptable salt thereof, a hydrate thereof or a solvate thereof as an active ingredient for antioxidation.

In an exemplary embodiment, the theasinensin A may be purchased commercially or may be prepared. In an exemplary embodiment, the theasinensin A may be prepared using a laccase. For example, it may be prepared by a method comprising: a step of reacting epigallocatechin gallate and a laccase at pH 4.5-5.5; and a step of obtaining theasinensin A by heat-treating the reaction product. However, theasinensin A prepared by any method may be used without being limited thereto. In an exemplary embodiment, the laccase may be a laccase derived from *Trametes versicolor*. Also, in an exemplary embodiment, the heat treatment may be performed at 75-95° C., specifically at 80-90° C. More specifically, the theasinensin A may be prepared by a method comprising: a step of adding epigallocatechin gallate and a laccase to a citric acetate buffer and preparing dehydrotheasinensin A, which is an intermediate dimer, by performing reaction under a weakly acidic condition for about 30-90 minutes; and a step of converting the intermediate dimer to theasinensin A by heat-treating the intermediate dimer and obtaining theasinensin A by separating and purifying the same.

In an exemplary embodiment, the cosmetic composition according to the present disclosure may be formulated by comprising a cosmetologically or dermatologically acceptable medium or base. It may be provided as any topically applicable formulation, for example, in the form of a solution, a gel, a solid, an anhydrous paste, an oil-in-water emulsion, suspension, a microemulsion, a microcapsule, a microgranule, an ionic (liposomal) or non-ionic vesicular dispersion, a cream, a lotion, a powder, an ointment, a spray or a concealer stick. In addition, it may be used in the form of a foam or an aerosol composition further comprising a compressed propellant. These compositions may be prepared according to common methods in the art.

In an exemplary embodiment, the the cosmetic composition according to the present disclosure may comprise, in addition to the active ingredient, other ingredients that can provide synergistic effect to the main effect within a range not negatively affecting the main effect. The ingredients other than the active ingredient of the present disclosure may be adequately selected by those skilled in the art in consideration of the formulation of the cosmetic composition or the purpose of use. In addition, the cosmetic composition according to an exemplary embodiment of the present disclosure may comprise, in addition to the above-described ingredients, other ingredients commonly comprised in a cosmetic composition, if necessary. Examples may comprise a moisturizer, an emollient, an organic or inorganic pigment, an organic powder, a UV absorbent, an antiseptic, a sterilizer, an antioxidant, a plant extract, a pH-adjusting agent, an alcohol, a colorant, a flavor, a blood circulation accelerator, a cooling agent, an antiperspirant, purified water, etc. The ingredients that may be comprised in the cosmetic composition of the present disclosure are not limited thereto and those ingredients may be comprised in a range not negatively affecting the purpose and effect of the present disclosure.

The composition according to an exemplary embodiment of the present disclosure may be a food composition comprising the active ingredient.

For example, it may be processed into a functional food comprising the active ingredient, such as fermented milk, cheese, yogurt, juice, probiotics, health food, etc. and may be used in the form of various food additives. In an exemplary embodiment, the composition may be a composition for health food. In an exemplary embodiment, the composition for health food may be formulated as a pill, a capsule, a tablet, a granule, a caramel, a drink, etc. In another exemplary embodiment, it may be processed in the form of a liquid, a powder, a granule, a tablet, a tea bag, etc. The composition may be administered through various methods such as simple drinking, administration by injection, spraying, squeezing, etc. The composition may comprise other ingredients that can provide synergistic effect to the main effect of the present disclosure within a range not negatively affecting the main effect. For example, it may comprise additives such as a flavor, a colorant, a sterilizer, an antioxidant, antiseptic, a moisturizer, a thickener, a mineral, an emulsifier, a synthetic polymer, etc. for improvement of physical properties. In addition, it may further comprise auxiliary ingredients such as a water-soluble vitamin, an oil-soluble vitamin, a polypeptide, a polysaccharide, a seaweed extract, etc. These ingredients may be adequately selected by those skilled in the art in consideration of the formulation or the purpose of use, and the addition amount may be selected within a range not negatively affecting the purpose and effect of the present disclosure. For example, the addition amount of those ingredients may be 0.0001-99.9 wt % based on the total weight of the composition.

The composition according to an exemplary embodiment of the present disclosure may be a pharmaceutical composition comprising the active ingredient. The pharmaceutical composition may further comprise a pharmaceutical adjuvant such as an antiseptic, a stabilizer, a wetting agent, an emulsification accelerator, a salt and/or buffer for control of osmotic pressure, etc. and other therapeutically useful substances.

In an exemplary embodiment, the pharmaceutical composition may be a formulation for oral administration, and the formulation for oral administration may be, for example, a tablet, a pill, a hard or soft capsule, a liquid, a suspension, an emulsion, a syrup, a powder, a dust, a fine granule, a granule, a pellet, etc. These formulations may comprise, in addition to the active ingredient, a surfactant, a diluent (e.g., lactose, dextrose, sucrose, mannitol, sorbitol, cellulose and glycine), a glidant (e.g., silica, talc, stearic acid and its magnesium or calcium salt and polyethylene glycol). The tablet may also comprise a binder such as magnesium aluminum silicate, starch paste, gelatin, tragacanth, methyl cellulose, sodium carboxymethyl cellulose and polyvinylpyrrolidone, and may comprise in some cases a disintegrant such as starch, agar, alginic acid or its sodium salt, or a pharmaceutical additive such as an absorbent, a colorant, a flavorant, a sweetener, etc. The tablet may be prepared by a common mixing, granulation or coating method.

In an exemplary embodiment, the pharmaceutical composition may be a formulation for parenteral administration, and the formulation for parenteral administration may be a formulation for rectal, topical, subcutaneous or transdermal administration. For example, the formulation may be an injection, a medicinal drop, an ointment, a lotion, a gel, a cream, a spray, a suspension, an emulsion, a suppository, a patch, etc., although not being limited thereto.

In an exemplary embodiment, the administration dosage of the pharmaceutical composition will vary depending on the age, sex and body weight of a subject to be treated, the particular disease or pathological condition to be treated, the severity of the disease or pathological condition, administration route and the discretion of a prescriber. The determination of the administration dosage based on these factors is within the level of those skilled in the art. For example, the administration dosage may be from 1 mg/kg/day to 10 g/kg/day or 5-100 mg/kg/day. However, the administration dosage does not limit the scope of the present disclosure in any way.

MODE FOR INVENTION

Hereinafter, the present disclosure will be described in detail through examples, comparative examples and test examples. However, the following examples, comparative examples and test examples are for illustrative purposes only and it will be obvious to those having ordinary knowledge in the art that the scope of the present disclosure is not limited by them.

PREPARATION EXAMPLE

As an exemplary embodiment of the present disclosure, theasinensin A (TSA) as an EGCG dimer used as an active ingredient was prepared as follows.

First, 10 mM of epigallocatechin gallate (EGCG, CAS Number 989-51-5, Sigma Product No. E4143) and one unit of a laccase derived from *Trametes versicolor* (CAS Number 80498-15-3, Enzyme Commission (EC) Number 1.10.3.2, Sigma Product No. 38429) were added to 50 mM of a pH 5.0 citric acetate buffer to a total volume of 100 mL. After preparing an intermediate dimer dehydrotheasinensin A by conducting reaction for 1 hour while stirring at 150 rpm, the intermediate dimer was converted to theasinensin A by performing heat treatment at 85° C. Then, the product was separated and purified using Sephadex LH-20 and a C18 column. The conversion rate to theasinensin A was about 67%, and the final yield of separation and purification using the column was 16.6 (wt/wt %).

[Test Example 1] Evaluation of Stability

The following experiment was conducted to investigate the stability of theasinensin A as an active ingredient.

First, a solubilized formulation comprising the theasinensin A prepared in Preparation Example (Example 1) and a solubilized formulation comprising EGCG (Comparative Example 1) were prepared with the following compositions.

TABLE 1

|  | Example 1 | Comparative Example 1 |
|---|---|---|
| Theasinensin A | 0.02 | 0 |
| EGCG | 0 | 0.02 |

TABLE 1-continued

|  | Example 1 | Comparative Example 1 |
|---|---|---|
| Glycerin | 15 | 15 |
| Purified water (D.I. water) | 79.86 | 79.86 |
| Ethylenediaminetetraacetic acid (EDTA) | 0.02 | 0.02 |
| Butylene glycol | 5 | 5 |
| Phenoxyethanol | 0.05 | 0.05 |
| Sensiva SC50 | 0.05 | 0.05 |
| Total (wt %) | 100 | 100 |

Then, the titer of theasinensin A or EGCG remaining in the formulations of Example 1 and Comparative Example 1 was analyzed by high-performance liquid chromatography (HPLC) with 1-week intervals. Specifically, after storing 10 mL of each composition of Example 1 and Comparative Example 1 at 25° C. and sonicating the same with 1-week intervals after diluting 10 fold with methanol followed by filtering, the content was analyzed by HPLC.

Figure 1:
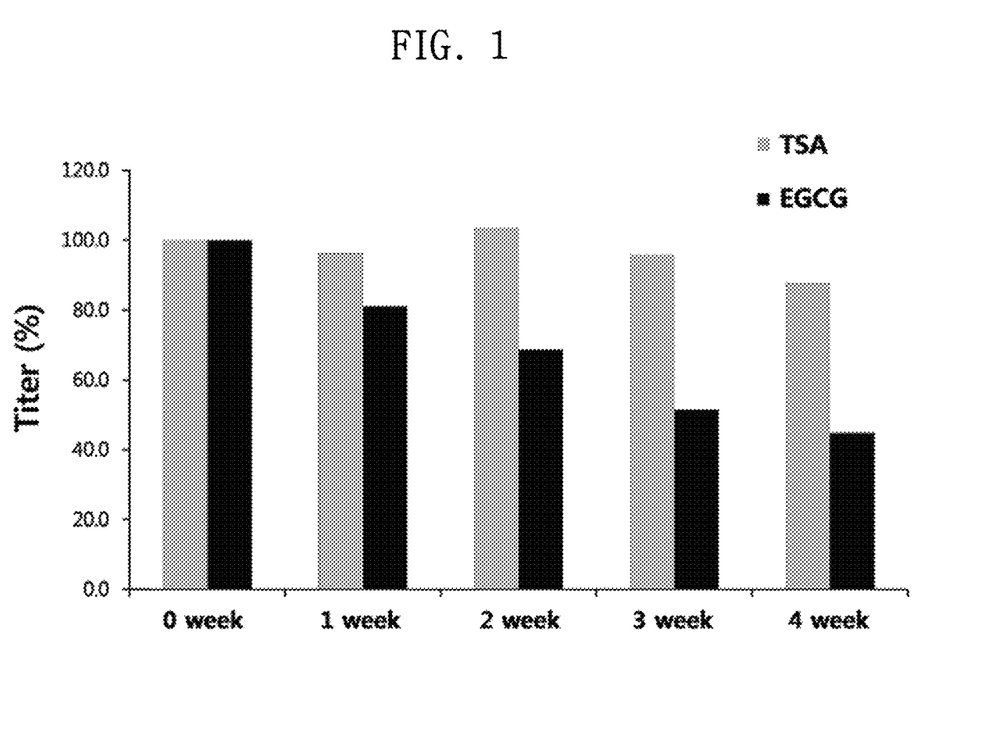
FIG. 1 shows a result of comparing the stability of theasinensin A (TSA) as an example of the present disclosure and epigallocatechin gallate (EGCG) as a comparative example in solubilized formulations.

As shown in FIG. 1, whereas the amount of theasinensin A remaining in the solubilized formulation of Example 1 about 4 weeks later was about 87 wt % or more of the total amount of theasinensin A used, the formulation of Comparative Example 1 wherein EGCG was used as the active ingredient was very unstable, with the content of EGCG remaining in the solubilized formulation being less than 80 wt % of the total amount of EGCG used 1 week later and less than 40 wt % 4 weeks later. This means that the composition of the present disclosure comprising theasinensin A, which is an oxidized form, as an active ingredient, has very superior formulation stability as compared to the composition comprising EGCG which is unstable against oxidation.

[Test Example 2] Evaluation of Antioxidant Effect

For investigation of the antioxidant effect of theasinensin A, the effect of inhibiting 2,2-diphenyl-1-picrylhydrazyl (DPPH) was tested as follows.

The 2,2-diphenyl-1-picrylhydrazyl (DPPH, Sigma D9132) radical dissolved in an organic solvent has the maximum absorbance at 515 nm. Since an antioxidant substance scavenges the DPPH radical and turns it colorless, antioxidant effect can be compared by measuring the DPPH radical-scavenging activity of theasinensin A through DPPH assay.

First, theasinensin A (TSA) was dissolved in ethanol such that the concentration of the theasinensin A (TSA) was 0.3125, 0.625, 1.25, 2.5, 5 and 10 ppm, respectively. The solutions of different concentrations were added to a 96-well plate, 10 µL each. Then, after adding 190 µL of 100 µM DPPH completely dissolved in ethanol to each solution and storing at 37° C. for 30 minutes, absorbance was measured at 515 nm.

DPPH assay was conducted in the same manner for 0.625, 1.25, 2.5, 5 and 10 ppm of vitamin C (Vit.C) as positive control groups and a negative control group (N.T.) not treated with theasinensin A (TSA) or vitamin C (Vit.C).

Figure 2:
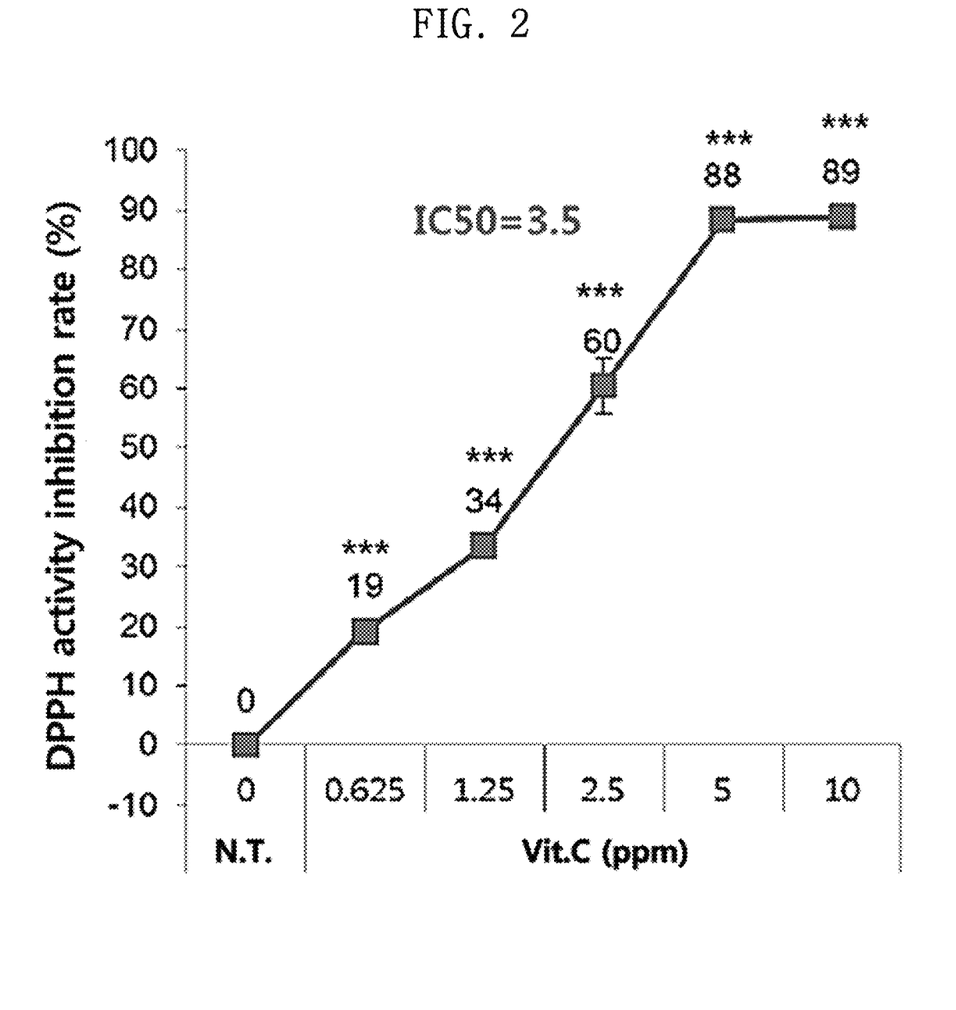
FIG. 2 shows a result of measuring the inhibition of DPPH activity depending on the concentration of vitamin C (Vit.C) as a comparative example of the present disclosure.
Figure 3:
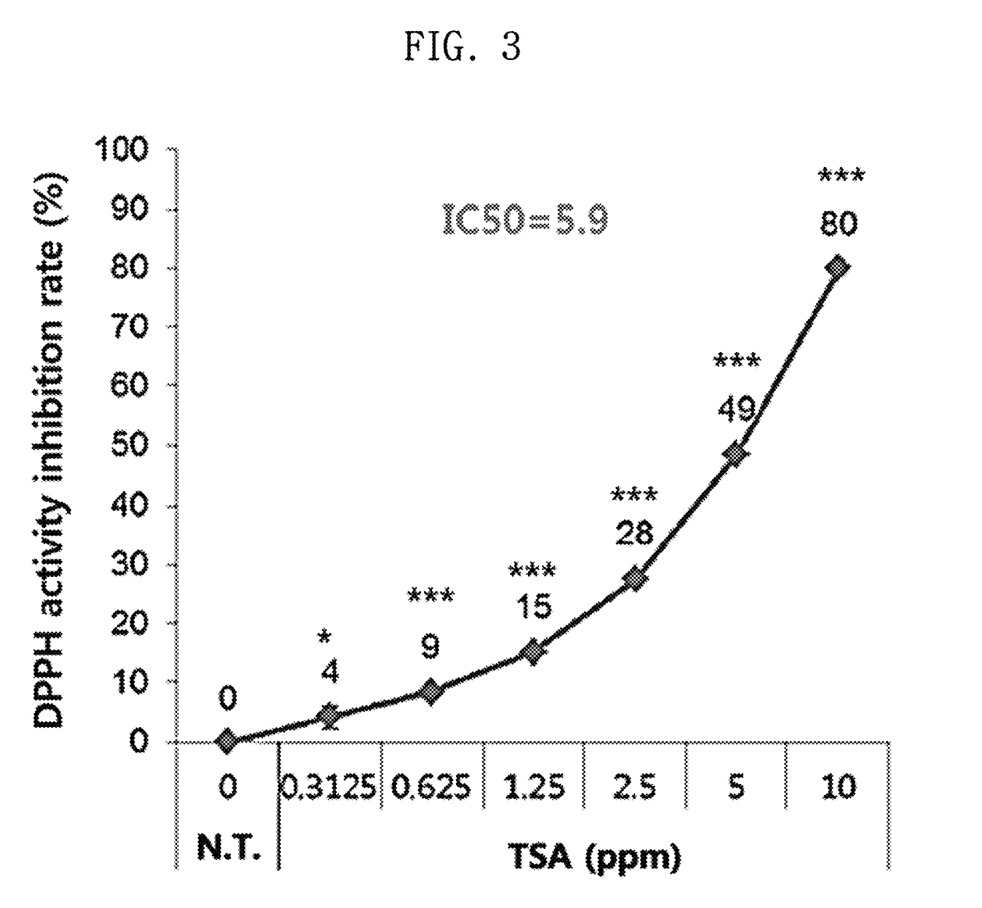
FIG. 3 shows a result of measuring the inhibition of DPPH activity depending on the concentration of theasinensin A (TSA) as an example of the present disclosure.

The result of evaluating the antioxidant effect of the positive control group vitamin C and theasinensin A is shown in FIG. 2 and FIG. 3, respectively. Theasinensin A showed almost comparable result as the positive control group vitamin C which is known to have very superior antioxidant. Specifically, theasinensin A showed significant antioxidant effect in a concentration-dependent manner, with $IC_{50}$=5.9 ppm, and inhibited DPPH activity significantly at a concentration of 0.3 ppm (0.0003 wt %) or higher.

[Test Example 3] Evaluation of Reducing Skin Wrinkles and Enhancing Skin Elasticity For investigation of the effect of reducing skin wrinkles and enhancing skin elasticity of theasinensin A, the effect of inhibiting the expression of matrix metalloproteinase-1 (MMP-1), which is a collagenase in the human body, was tested as follows.

First, a cell culture was prepared by treating UVB-irradiated HS68 cells (ATCC, Cat No CRL-1635) with the theasinensin A prepared in Preparation Example at 2.5, 5 or 10 ppm. After culturing HS68 cells (ATCC, Cat No CRL-1635) in a separate medium and adding phosphate-buffered saline (PBS) thereto after removing the medium, UVB was irradiated with an intensity of 30 mJ/cm$^2$. The UVB-irradiated cells were treated with the previously prepared theasinensin A-treated culture and cultured for 48 hours in an incubator. After recovering the culture, MMP-1 expression level was measured using a MMP-1 ELISA kit (Amersham, RPN2610).

Figure 4:
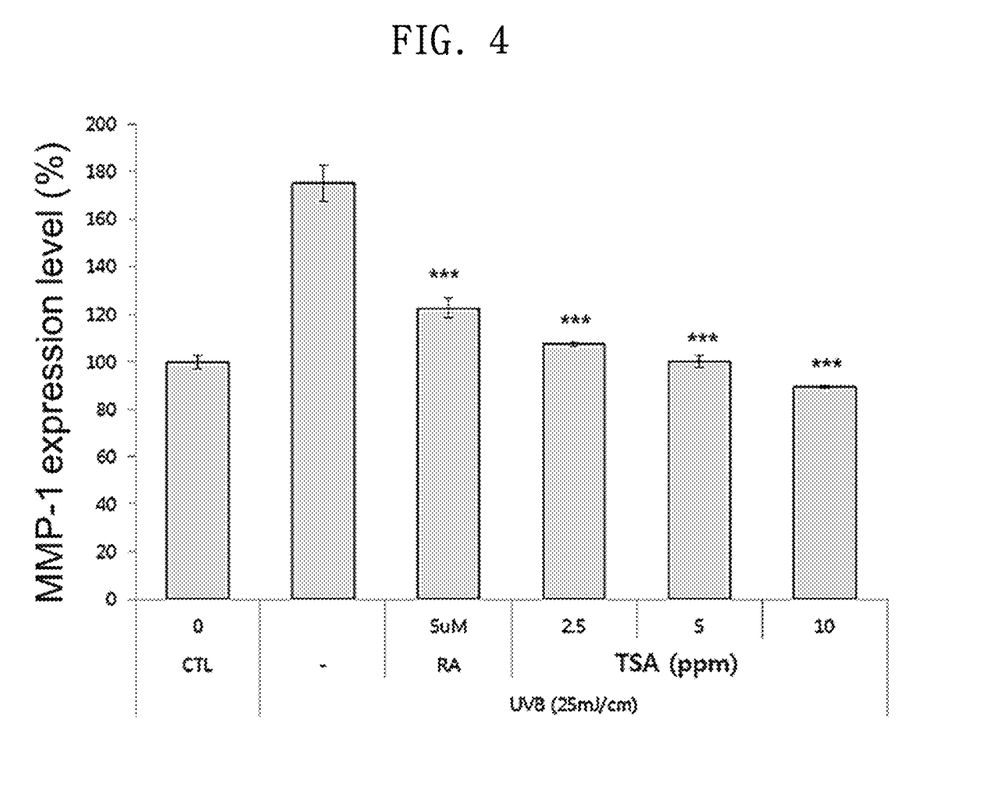
FIG. 4 shows a result of measuring MMP-1 expression level depending on the concentration of theasinensin A (TSA) as an example of the present disclosure.

As shown in FIG. 4, theasinensin A inhibited the expression of MMP-1 in the UVB-irradiated HS68 cells significantly in a concentration-dependent manner by about 50% or more. The MMP-1 expression level was inhibited significantly at concentrations of 2.5 ppm (0.0025 wt %) or higher, which suggests that theasinensin A provides the effect of reducing skin wrinkles and enhancing skin elasticity by inhibiting the degradation of collagen in skin.

[Test Example 4] Evaluation of Skin-Brightening Effect

For investigation of the skin-brightening effect of theasinensin A, the effect of inhibiting intra/extracellular melanin production was tested as follows.

First, after treating B16 cells (ATCC, Cat No CRL-6475) with 200 nM of α-melanocyte-stimulating hormone (α-MSH) and with theasinensin A as an example of the present disclosure or EGCG as a comparative example at nontoxic concentrations of 10 ppm or lower (2.5, 5 or 10 ppm), the intracellular and extracellular melanin contents 72 hours after the treatment were measured by correcting to the protein contents, and represented as % of melanin contents with respect to a non-theasinensin A-treated control group.

Figure 5:
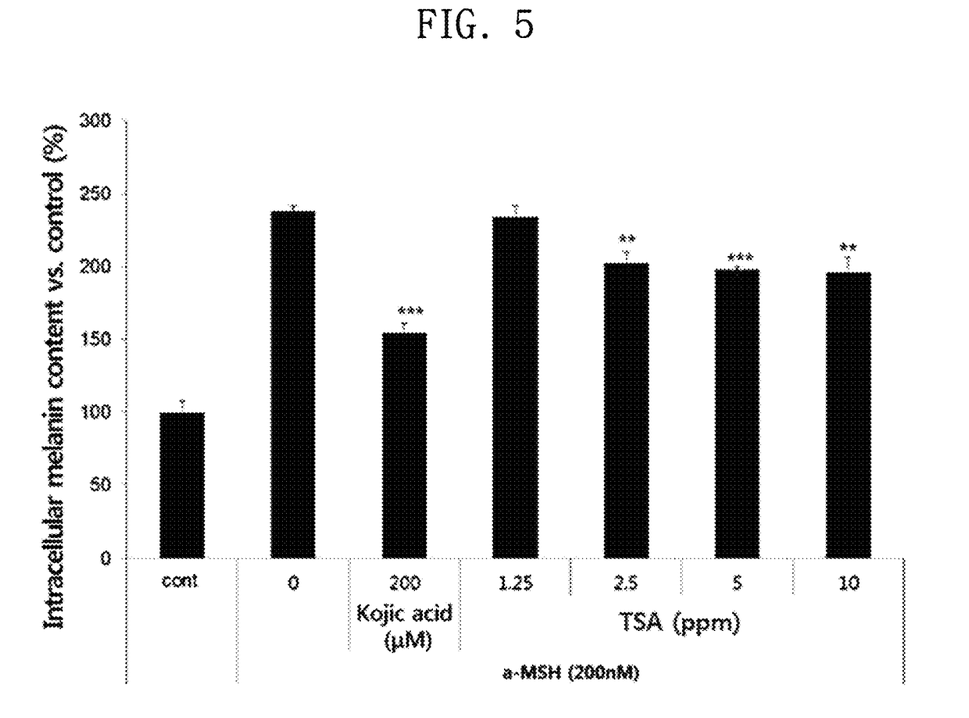
FIG. 5 shows a result of measuring the inhibition of intracellular melanin content by theasinensin A (TSA) as an example of the present disclosure (p value; *<0.05, <0.01, *<0.001 vs. only α-MSH-treated group).
Figure 6:
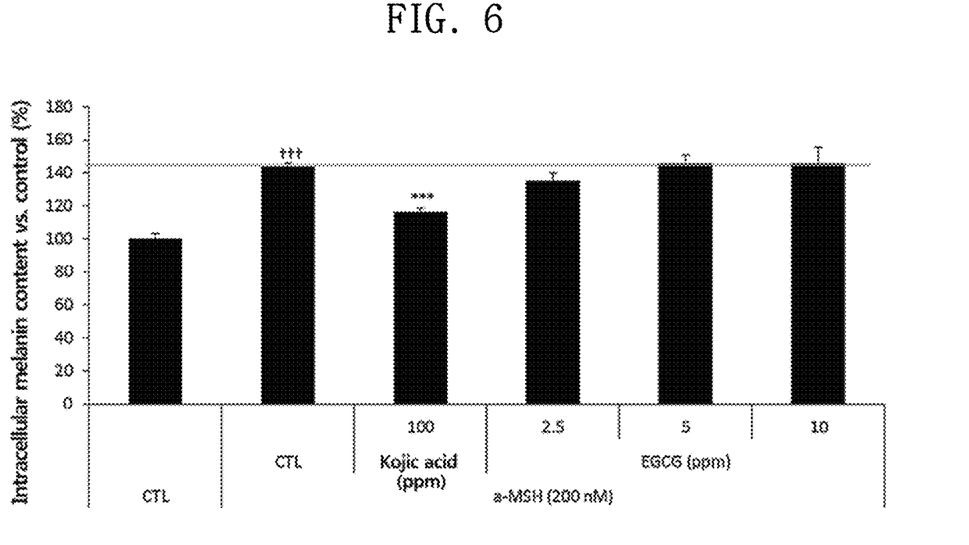
FIG. 6 shows a result of measuring the inhibition of intracellular melanin content by epigallocatechin gallate (EGCG) as a comparative example of the present disclosure.
Figure 7:
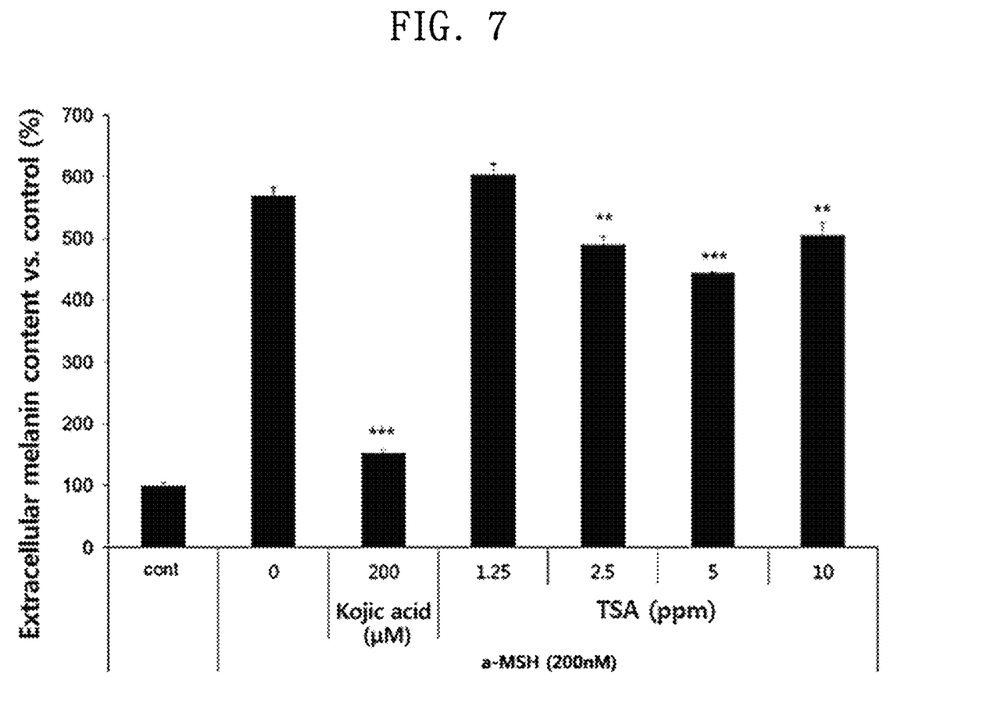
FIG. 7 shows a result of measuring the inhibition of extracellular melanin content by theasinensin A (TSA) as an example of the present disclosure (p value; *<0.05, <0.01, *<0.001 vs. only α-MSH-treated group).
Figure 8:
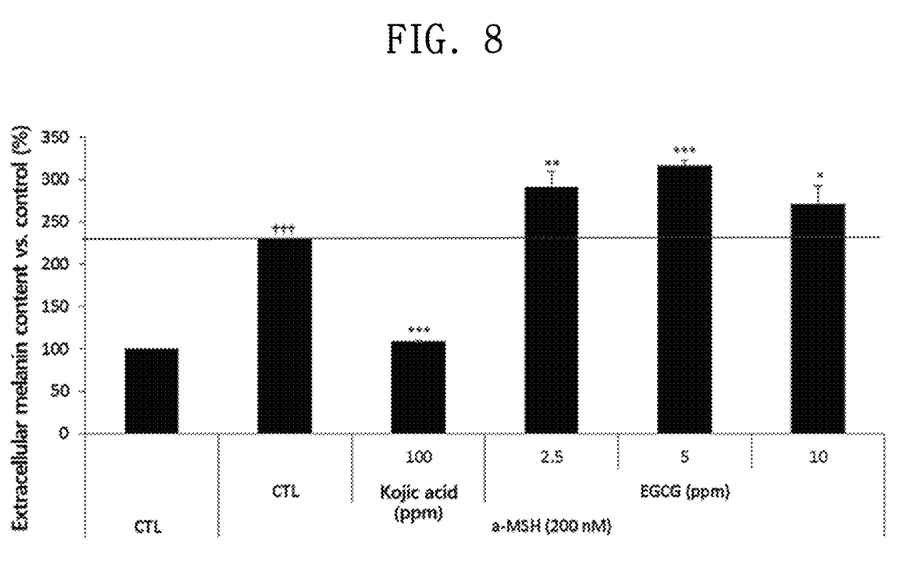
FIG. 8 shows a result of measuring the inhibition of extracellular melanin content by epigallocatechin gallate (EGCG) as a comparative example of the present disclosure.

The intracellular melanin content is shown in FIG. 5 (TSA) and FIG. 6 (EGCG), and the extracellular melanin content is shown in FIG. 7 (TSA) and FIG. 8 (EGCG).

As shown in FIG. 6 and FIG. 8, EGCG did not exhibit skin-brightening effect as compared to the control group treated only with α-MSH because the melanin content was increased both inside and outside the cells.

In contrast, as shown in FIG. 5 and FIG. 7, theasinensin A as an example of the present disclosure was confirmed to have skin-brightening effect because it resulted in decreased melanin content as compared to the control group treated only with α-MSH. In particular, it exhibited superior skin-brightening effect with about 30% of melanin production inhibition at 10 ppm (0.01 wt %).

Hereinafter, formulation examples of the composition according to an exemplary embodiment of the present disclosure are described. However, the following examples are only for the purpose of description and are not intended to limit the present disclosure.

[Formulation Example 1] Softening Lotion (Skin Lotion)

A softening lotion was prepared with the composition described in the following table according to a common method.

TABLE 2

| Ingredients | Contents (wt %) |
| --- | --- |
| Theasinensin A | 0.1 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Antiseptic, colorant and flavor | Adequate |
| Purified water | Balance |

[Formulation Example 2] Nourishing Lotion (Milk Lotion)

A nourishing lotion was prepared with the composition described in the following table according to a common method.

TABLE 3

| Ingredients | Contents (wt %) |
| --- | --- |
| Theasinensin A | 0.1 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Antiseptic, colorant and flavor | Adequate |
| purified water | Balance |

[Formulation Example 3] Massage Cream

A massage cream was prepared with the composition described in the following table according to a common method.

TABLE 4

| Ingredients | Contents (wt %) |
| --- | --- |
| Theasinensin A | 0.1 |
| Glycerin | 8.0 |
| Butylene glycol | 4.0 |
| Liquid paraffin | 45.0 |
| Beta-glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |

TABLE 4-continued

| Ingredients | Contents (wt %) |
| --- | --- |
| Antiseptic, colorant and flavor | Adequate |
| Purified water | Balance |

[Formulation Example 4] Tablet

A tablet was prepared according to a common tablet preparation method after mixing 100 mg of theasinensin A, 400 mg of lactose, 400 mg of corn starch and 2 mg magnesium stearate.

[Formulation Example 5] Capsule

After mixing 100 mg of theasinensin A, 400 mg of lactose, 400 mg of corn starch and 2 mg of magnesium stearate, a capsule was prepared by filling the mixture in a gelatin capsule according to a common capsule preparation method.

[Formulation Example 6] Granule

After mixing 50 mg of theasinensin A, 250 mg of anhydrous crystalline glucose and 550 mg of starch and forming the mixture into a granule using a fluidized-bed granulator, the granule was filled in a pouch.

[Formulation Example 7] Drink

After mixing 50 mg of theasinensin A, 10 g of glucose, 0.6 g of citric acid and 25 g of oligosaccharide syrup, 300 mL of purified water was added and 200 mL of the mixture was filled per bottle. Then, a drink was prepared by sterilizing at 130° C. for 4-5 seconds.

[Formulation Example 8] Caramel

A caramel was prepared by mixing 50 mg of theasinensin A, 1.8 g of corn syrup, 0.5 g of skim milk, 0.5 g of soybean lecithin, 0.6 g of butter, 0.4 g of hydrogenated vegetable oil, 1.4 g of sugar, 0.58 g of margarine and 20 mg of table salt.

[Formulation Example 9] Health Food

TABLE 5

| Ingredients | Contents |
| --- | --- |
| Theasinensin A | 100 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |

TABLE 5-continued

| Ingredients | Contents |
| --- | --- |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

Although the above-described compositions of vitamin and mineral mixtures are presented as relatively suitable examples for health food, they may be changed as desired. After mixing the above-described ingredients and preparing a granule according to a common health food preparation method, a health food composition may be prepared according to a common method.

[Formulation Example 10] Health Beverage

TABLE 6

| Ingredients | Contents |
| --- | --- |
| Theasinensin A | 10 mg |
| Citric acid | 1000 mg |
| Oligosaccharide | 100 g |
| Japanese apricot concentrate | 2 g |
| Taurine | 1 g |
| Purified water | Balance |
| Total volume | 900 mL |

After mixing the above-described ingredients by adding purified water to a total volume of 900 mL, stirring and heating the mixture at 85° C. for about 1 hour, the prepared solution was filtered, transferred to a sterilized 2-L container and then stored in a refrigerator for later use in preparation of a health beverage composition.

[Formulation Example 11] Injection

An injection was prepared with the composition described in the following table according to a common method.

TABLE 7

| Ingredients | Contents |
| --- | --- |
| Theasinensin A | 10-50 mg |
| Sterilized distilled water for injection | Adequate |
| pH-adjusting agent | Adequate |

The present disclosure may provide the following exemplary embodiments.

A first exemplary embodiment may provide a cosmetic composition comprising theasinensin A, an enantiomer thereof, a pharmaceutically acceptable salt thereof, a hydrate thereof or a solvate thereof as an active ingredient.

A second exemplary embodiment may provide the cosmetic composition according to the first exemplary embodiment, wherein the theasinensin A has a structure of Chemical Formula 1.

[Chemical Formula 1]

A third exemplary embodiment may provide the cosmetic composition according to the first or second exemplary embodiment, wherein the theasinensin A is a dimer of epigallocatechin gallate.

A fourth exemplary embodiment may provide the cosmetic composition according to one or more of the first to third exemplary embodiments, which is for reducing skin wrinkles or enhancing skin elasticity.

A fifth exemplary embodiment may provide the cosmetic composition according to one or more of the first to fourth exemplary embodiments, which is for brightening skin.

A sixth exemplary embodiment may provide the cosmetic composition according to one or more of the first to fifth exemplary embodiments, which is for anti oxidation.

A seventh exemplary embodiment may provide the cosmetic composition according to one or more of the first to sixth exemplary embodiments, which comprises the active ingredient in an amount of 0.001-1 wt % based on the total weight of the composition.

An eighth exemplary embodiment may provide the cosmetic composition according to one or more of the first to seventh exemplary embodiments, wherein the administration dosage of the active ingredient is from 0.1 mg/kg/day to 10 g/kg/day.

A ninth exemplary embodiment may provide the cosmetic composition according to one or more of the first to eighth exemplary embodiments, wherein the theasinensin A is prepared by a method comprising: a step of reacting epigallocatechin gallate with a laccase at pH 4.5-5.5; and a step of obtaining theasinensin A by heat-treating the reaction product.

The above exemplary embodiments are presented for illustration of the present disclosure, but the description does not limit the scope of the present disclosure. Accordingly, various modifications, changes and substitution may be made by those of ordinary skill in the art without departing from the meaning and scope of the present disclosure.

The invention claimed is:

1. A method for brightening skin by inhibiting melanin production, which comprises applying an effective amount of a cosmetic composition A cosmetic composition comprising theasinensin A, an enantiomer thereof, a pharmaceutically acceptable salt thereof, or a hydrate thereof as an active ingredient to a subject in need thereof, wherein the application of the cosmetic composition inhibits melanin production in the skin.

2. The method according to claim 1, wherein the theasinensin A, an enantiomer thereof, a pharmaceutically acceptable salt thereof or a hydrate thereof is contained in an amount of 0.001-1 wt % based on the total weight of the composition.

3. The method according to claim 1, wherein the application dosage of the theasinensin A, an enantiomer thereof, a pharmaceutically acceptable salt thereof, or a hydrate thereof is from 0.1 mg/kg/day to 10 g/kg/day.

4. The method according to claim 1, wherein the theasinensin A has a structure of Chemical Formula 1:

[Chemical Formula 1]

5. The method according to claim 1, wherein the theasinensin A is a dimer of epigallocatechin gallate of the following Chemical Formula 2:

[Chemical Formula 2]

* * * * *